United States Patent [19]

Bucovaz et al.

[11] 4,234,476
[45] Nov. 18, 1980

[54] APPLICATION OF PROTEIN-PROTEIN INTERACTION AS AN ASSAY FOR THE DETECTION OF CANCER

[75] Inventors: Edsel T. Bucovaz; John C. Morrison, both of Memphis; William C. Morrison, Germantown; Walter D. Whybrew, Memphis, all of Tenn.

[73] Assignee: Research Corporation, New York, N.Y.

[21] Appl. No.: 884,288

[22] Filed: Mar. 7, 1978

Related U.S. Application Data

[62] Division of Ser. No. 727,633, Sep. 29, 1976, Pat. No. 4,160,817.

[51] Int. Cl.$^2$ ............................ A23J 1/18; C07G 7/03
[52] U.S. Cl. ............................... 260/112 R; 424/177; 426/60
[58] Field of Search ................... 260/112 R; 426/60; 424/177

[56] References Cited

U.S. PATENT DOCUMENTS

| | | | |
|---|---|---|---|
| 3,663,684 | 5/1972 | Freedman et al. | 424/1 |
| 3,697,638 | 10/1972 | Hansen | 424/1 |
| 3,869,436 | 3/1975 | Albinsson | 424/177 X |
| 3,888,839 | 6/1975 | Newell et al. | 260/112 R |
| 3,935,072 | 1/1976 | Chibata et al. | 260/112 R X |
| 4,079,048 | 3/1978 | Chao | 260/112 R |
| 4,080,260 | 3/1978 | Chao | 260/112 R X |

FOREIGN PATENT DOCUMENTS 1388719  3/1975  United Kingdom .

OTHER PUBLICATIONS

Bucovaz et al., *Proc. Am. Assoc. Cancer Research*, vol. 16 (1975), p. 80, Abstract #318.

*Primary Examiner*—Walter C. Danison
*Attorney, Agent, or Firm*—Oblon, Fisher, Spivak, McClelland & Maier

[57] ABSTRACT

A specific type of protein, which has been designated B-protein (Bucovaz-protein), is present in most serum of individuals with cancer. The B-protein interacts with a low molecular weight protein component, which is released by the coenzyme A-synthesizing protein complex (CoA-SPC) of Bakers' yeast during the course of CoA synthesis. This low molecular weight protein, for purposes of identification, is referred to as binding protein. The binding protein has a molecular weight of 10,000 to 15,000. Interaction of radioactively labeled binding protein of CoA-SPC with the B-protein of serum provides a marker for the detection of cancer. Of 3005 serums assayed, which included 908 patients diagnosed as having cancer, the B-protein assay agreed with the clinical diagnosis in more than 89% of the cases.

1 Claim, 2 Drawing Figures

4,234,476

APPLICATION OF PROTEIN-PROTEIN INTERACTION AS AN ASSAY FOR THE DETECTION OF CANCER

This is a division of application Ser. No. 727,633 filed Sept. 29, 1976 now U.S. Pat. No. 4,160,817.

BACKGROUND OF THE INVENTION

1. Field of the Invention:

This invention relates to a method of detecting the presence of cancer and to a reagent for use therein. Moreover, it relates to a novel low molecular weight binding protein for use in the cancer detection method and to a method of preparation of the binding protein and preparation of the CoA-SPC.

2. Description of the Prior Art:

Early detection stands today as one of the most effective means for combating cancer. During the past several years, numerous methods have been reported for the detection of cancer. Some of these have been physical, while others are chemical in nature. Most of the physical methods, such as mammography and X-ray, have had reasonable success in the detection of cancer, but the hazards of radiation may be greater than is generally believed, and may outweigh their value.

Of the chemical assays (see, for example, U.S. Pat. Nos. 3,673,410, 3,697,638 and 3,663,684), the carcinoembryonic antigen (CEA) assay (Gold and Freedman, J. Exp. Med., 121, 439–462 (1965); Gold and Freedman, J. Exp. Med., 122, 467–481 (1965); and Thomson et al,. Proc. Nat. Acad. Sci., 64, 161–167 (1969)) has been most extensively publicized, and has been subject of extensive investigation. However, the CEA assay appears to have its greatest potential value in the area of cancer management and not detection. There are mixed opinions in regard to the usefulness of the CEA assay for the routine diagnosis of cancer in the clinic and in population screening (Stevens et al., Br. J. Cancer, 32, 147–151 (1975)).

As a result, early detection of cancer generally must rely on the early appearance of easily observable symptoms such as skin lesions, lumps etc.. Moreover, in many cases detection of even such symptoms must rely on a fortuitous observation by the patient himself.

Consequently, there is a critical need for a reliable method of screening patients for the presence of cancer.

SUMMARY OF THE INVENTION

Accordingly, it is one object of the present invention to provide a method and reagent for the detection of cancer.

It is another object of this invention to provide a method for detection of a specific protein (B-protein) whose presence in blood serum is associated with the presence of cancer.

It is a further object of this invention to provide a binding protein and reagent containing the same which is useful in the detection of the B-protein.

It is also an object of this invention to provide a method of preparation of a CoA-SPC Bakers' yeast extract from which the binding protein is released.

It is still another object of the invention to provide a method of preparation of the binding protein.

These and other objects of the invention as will hereinafter become clear have been attained by providing a method for detection of cancer in humans which comprises detecting the presence of B-protein in blood serum. Presence of the B-protein in serum is shown to be indicative of the presence of cancer. Detection of B-protein is accomplished by addition to the serum of a reagent containing a radioactively tagged low molecular weight binding protein. This binding protein binds to the B-protein, and the B-protein/bound protein complex can be detected by radioactivity counting techniques. The novel low molecular weight binding protein is extracted from the coenzyme A-synthesizing protein complex (CoA-SPC) of Bakers' yeast during interaction with substrates therefor.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
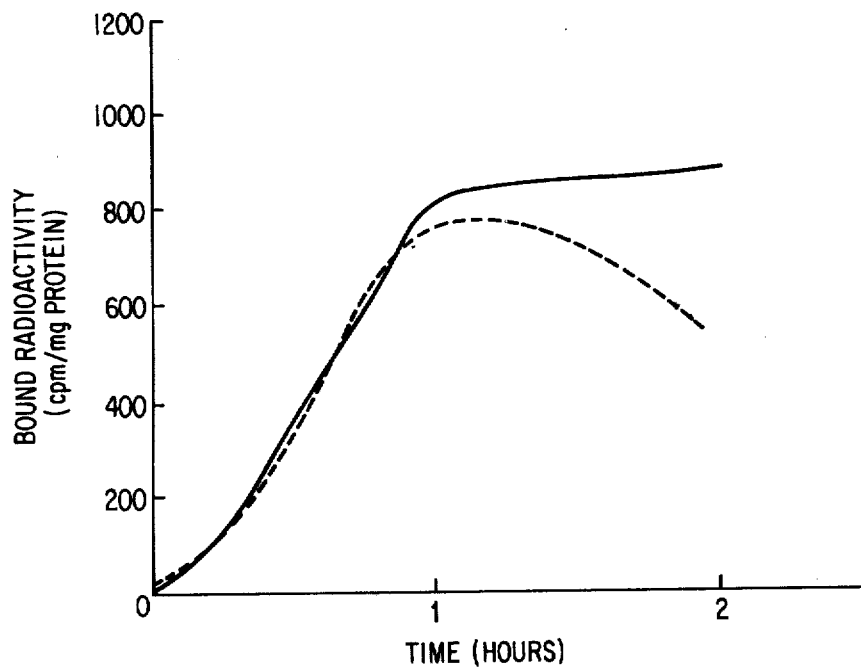
FIG. 1 shows the time course of CoA-SPC bound radioactivity for two CoA-SPC preparations.

A specific type of protein normally present in human serum has been observed to interact with a low molecular weight protein component released from the coenzyme A-synthesizing protein complex (CoA-SPC) of Bakers' yeast. In cancer patients the serum protein is modified, or a protein with somewhat similiar characteristics is produced and released into the blood, which also interacts with the low molecular weight protein of yeast. This protein found in the serum of individuals with cancer has tentatively been designated the Bucovaz-protein (B-protein). The source of B-protein is not known. It may be produced by the cancer cells, or possibly the presence of cancer cells triggers a particular immune system or some other system in the body which produces this protein component.

The normal protein and the B-protein have similar properties. Both interact with the binding protein mentioned above. Moreover, the B-protein of cancer patients and the specific protein present in the serum of all individuals migrate in an electrical field in the same general area as the γ-globulin fraction of human serum. Both proteins have a molecular weight of approximately 140,000–160,000, and have the same pattern of separation in a 3% to 10% continuous sucrose gradient. Also both proteins are precipitated by 50% saturation of the serum with $(NH_4)_2SO_4$. Furthermore, as the titer of B-protein in the serum of cancer patients increases, the amount of its normal counterpart appears to decrease in a proportional manner. Although present information is not adequate to make a definite statement, and without intending to limit this invention in any way, it is speculated that the B-protein represents a modification of the yet unidentified protein of normal serum which interacts with the binding protein of CoA-SPC. However, although the B-protein of cancer patients is similar to the serum protein present in individuals who do not have cancer, differences in the properties between the two are sufficient for separation and identification of the B-protein.

Any means of detecting the presence of B-protein and discrimintaing against normal protein can be used in this invention. A preferred method used herein involves the addition to a patient's serum sample of a reagent containing the specific low molecular weight binding protein described above in a radioactively tagged form. This binding protein is typically contained in a reagent comprising CoA-SPC. The released binding protein binds with both the normal protein and B-protein in the serum. Subsequent partial denaturation of the bound protein complexes serves to discriminate between the two types of proteins based upon solubility differences thereby induced.

Reference to certain properties of the CoA-SPC as a protein complex which synthesizes CoA has been made in the following:

1. Bucovaz, E. T., Sobhy, C. M., Morrison, W. C., Whybrew, W. D., Morrison, J. C., Wiser, W. L., Fish, S. A. and Fryer, J. E., "Conjugation of Cyclic Hydrocarbons with the Coenzyme A-Synthesizing Protein Complex of Bakers' Yeast," Proc. Am. Assoc. Cancer Research, 16(1975) *Abstract for oral presentation*
2. Sobhy, C. M., Whybrew, W. D., Morrison, J. C., Morrison, W. C., Wiser, W. L., Fish, S. A., Fryer, J. E. and Bucovaz, E. T., "Coenzyme A-Synthesis by a Protein Complex of Bakers' Yeast," Federation Proc. 34, 599 (1975). *Abstract for oral presentation*
3. Morrison, J. C., Morrison, W. C., Whybrew, W. D., Wiser, W. L. and Bucovaz, E. T., "Alteration of Coenzyme A-Synthesizing Protein Complex Activity Related to Cyclic Hydrocarbon Conjugation," IRCS, Med. Sci. 3, 23 (1975).
4. Morrison, J. C., Morrison, W. C., Whybrew, W. D., Wiser, W. L., and Bucovaz, E. T., "Alterations in Coenzyme A-Synthesizing Protein Complex Activity Related to Cyclic Hudrocarbon Conjugation," Southeastern Cancer Res. Assoc. (1975). *Abstract for oral presentation*
5. Morrison, W. C., Whybrew, W. D., Morrison, J. C., Fryer, J. E., Sobhy, C. M. and Bucovaz, E. T., "Alternant Functions of the Coenzyme A-Synthesizing Protein Complex of Bakers' Yeast," American Chemical Society (1975). *Abstract for oral presentation*
6. Rhoades, J. L., Morrison, W. C., Whybrew, W. D., Morrison, J. C., Fryer, J. E. and Bucovaz, E. T., "Modified Preparation of the Coenzyme A-Synthesizing Protein Complex of Bakers' Yeast," Southeast-Southwest Meeting, American Chemical Society (1975). *Abstract for oral presentation*
7. Bucovaz, E. T., Morrison, J. C., Morrison, W. C., Whybrew, W. D., "An Abnormal Protein Present in Human Serum of Pateints with Cancer can be Detected by Protein-Protein Interactions," 10th International Congress of Biochemistry (1976). *Abstract for oral presentation*
8. Bucovaz, E. T., Morrison, J. C., Rhoades, J. L., Morrison, W. C., Fryer, J. E. and Whybrew, W. D., "Purification of the Coenzyme A-Synthesizing Protein Complex of Bakers' Yeast," Amer. Society of Biol. Chemists (1976). *Abstract for oral presentation*
9. Morrison, J. C., Morrison, W. C., Whybrew, W. D., Wiser, W. C. and Bucovaz, E. T., "Coenzyme A-Synthesizing Protein Complex Activity Altered by Cyclic Hydrocarbon Conjugation," Proc. Am. Assoc. Cancer Research (1976). *Abstract for oral presentation*
10. Bucovaz, E. T., Morrison, J. C., Morrison, W. C. and Whybrew, W. D., "Protein-Protein Interaction Used as Assay for Detection of Abnormal Serum Protein of Patients with Cancer," Third International Symposium on Detection and Prevention of Cancer 464 (1976). *Abstract for oral presentation*
11. Bucovaz, E. T., Morrison, J. C., Morrison, W. C. and Whybrew, W. D., "Protein-Protein Interaction Used as Assay for Detection of Abnormal Serum Protein of Patients with Cancer," Third International Symposium on Detection and Prevention of Cancer, Proceedings (1976). *Publication, in press*
12. Bucovaz, E. T., Morrison, J. C., Morrison, W. C. and Whybrew, W. D., "Assay for the Detection of a Protein Component in the Serum of Individuals with Cancer," J. Tenn. Acad. of Sci. (1976). *Publication, in press*
13. Morrison, J. C., Whybrew, W. D., Morrison, W. C. and Bucovaz, E. T., "Application of Protein-Protein Interaction as an Assay for the Detection of Cancer," Amer. Chem. Society (1976). *Abstract for oral presentation*
14. Morrison, J. C., Whybrew, W. D., Morrison, W. C. and Bucovaz, E. T., "Detection of a Protein Component in the Serum of Individuals with Cancer," Amer. Chem. Society (1976). *Abstract for oral presentation*

The coenzyme A-synthesizing protein complex utilizes L-cysteine, D-pantothenic acid and ATP as substrates. The following explanation of the sequence of reactions leading to release of the aforementioned binding protein is of a theoretical nature only and is not meant to limit this invention in any way. The initial reaction catalyzed by the CoA-SPC is between the $\beta$-phosphorous group of ATP and the 4' hydroxyl group of pantothenic acid resulting in the formation of CoA-SPC bound ADP-4-pantothenic acid. The $\alpha$-amino group of cysteine then reacts with the carboxyl group of the pantothenic acid moiety. At the time of reaction, cysteine is decarboxylated forming CoA-SPC bound dephospho-CoA. Dephospho-CoA is either phosphorylated and released as CoA, or is hydrolyzed to yield what appears to be 4'-phosphopantetheine bound to a low molecular weight protein component of the CoA-SPC, which then detaches from the complex. The molecular weight of the binding protein is in the range of 8,000 to 18,000, and most probably 10,000 to 15,000 (weight average).

One function of the CoA-SPC apparently is the synthesis of CoA; the other may be associated with the synthesis of acylcarrier protein. The low molecular weight protein is suspected of being related to the latter of these two functions of CoA-SPC. In regard to the B-protein assay, the low molecular weight protein is what is referred to as the binding protein.

Two modes of preparation of the CoA-SPC complex is fully disclosed in references Nos. 11 and 12 cited above. These preparative techniques can be used to provide the CoA-SPC for the assay of this invention. These methods involve first freezing and subsequently thawing Bakers' yeast. The thawed yeast is then subjected to agitation whereby CoA-SPC is progressively released from its cellular structural affinities. The agitation can be provided by conventional techniques such as mechanical stirring or bubbling an inert gas, e.g., air, $CO_2$, $N_2$, etc. through the mixture. Many variations of this basic process are possible. Other methods of breaking the yeast cell, such as grinding, sonication or pressure have proven to be unsuccessful.

The specific procedure disclosed in reference 12 is as follows:

Bakers' yeast is crumbled into fine particles and frozen. For example, freezing can be performed for from 1 to 6 hours, preferably from 4 to 6 hours, in an ether (1.5–2.0 l)-$CO_2$(5–7 lbs, dry ice) mixture. The time and temperature of the freezing step are not critical. Commercially available Federal Brand and Fleischman yeast have been successfully utilized. The frozen yeast is allowed to thaw under ambient conditions to room temperature. If a freezing medium such as the $CO_2$/ether mentioned above is used, residual ether and $CO_2$ should be removed, e.g., by vacuum treatment to avoid denaturation of the protein. The thawed yeast is then agitated, e.g., by stirring to release CoA-SPC. If desirable, a stabilizing agent such as KCl or a similarly effective salt may be added. Typically, up to 15 g of KCl, preferably from 1 to 10 g, per pound of Bakers' yeast are added to the thawed homogenate. Typical Bakers' yeast samples range from 1 to 4 pounds, preferably from 2 to 3 pounds, but the sample size, of course, is not critical. The conditions used during the agitation step depend upon the rate of agitation and are chosen to effectively release the CoA-SPC without attendant denaturation of the enzyme and other proteins in the homogenate. Typical conditions comprise stirring for from 6 to 25 hours, preferably from 15 to 20 hours at a temperature of from 0° to 12° C., preferably 0° to 3° C. After stirring, the CoA-SPC-containing liquid is removed from the solid components in conventional fashion, e.g., by centrifuging for from 10 to 30 minutes at 6,000 to 8,000 xg. Subsequent conventional purification procedures can then be employed on the supernatant liquid. For instance, the CoA-SPC-containing liquid can be decanted through several (e.g., 3–6) folds of cheesecloth. Using such a procedure, about 350–375 ml of crude CoA-SPC extract has typically been obtained from a three pound sample of Bakers' yeast. The crude extract has been stored for one year at cryogenic temperatures of from approximately −90° to −100° C. without losing its capacity for synthesis of CoA and for release of the binding protein.

The procedure described in Reference 11 which is a modification of that described above, is a preferred method. It is similar to the method described in Reference 12, but in addition provides for the further purification of CoA-SPC. This method is as follows:

Bakers' yeast is crumbled, frozen and thawed as above. However, prior to the foregoing agitation step, the thawed yeast is subjected to a preagitation, wherein the aforementioned stabilizers may also be incorporated. This first agitation is provided to remove endogenous substrates from the yeast into the liquid phase, and not to effect release of significant amounts of CoA-SPC. Thus, it is generally applied for a much shorter period of time. For example, stirring for from 1–4 hours at temperatures such as 0° to 12° C. can be employed. The liquid phase is then removed, for example, by one or more centrifugations. The solid phase is then resuspended in aqueous solution. For example, Buffer A, defined hereinbelow, may be used. The resultant mixture is then agitated to release the CoA-SPC and subsequently treated as in the first method. This second agitation can be for a shorter period of time than used for the sole agitation in the first method. For example, stirring for from 11 to 13 hours can be used. The purified extract has been found to represent a 97.3-fold purification of the CoA-SPC.

One embodiment of the reagent of this invention comprises CoA-SPC and substrates thereof which interact with the extract to produce the binding protein. Such substrates include ATP or a salt thereof, such as the disodium salt, and the like; D-pantothenic acid or a salt thereof, such as the hemi-calcium salt, and the like; and L-cysteine or a salt thereof. These four components react to produce the binding protein. To speed up the reaction, the mixture may be incubated. The ratio of amounts of the components and the pH of the reagent are not critical as long as the binding protein is produced. A suitable pH range is from 6.2 to 7.6, preferably from 6.5 to 7.2. One specific formulation found to produce satisfactory results in the assay of this invention is as follows: from 0.01 to 0.1 ml, preferably 0.04 to 0.06 ml. of CoA-SPC; from 0.01 to 10 mM, preferably from 1.5 to 5 mM ATP or salt thereof; from 0.01 to 1.0 mM, preferably from 0.5 to 0.6 mM, D-pantothenic acid or salt thereof; and from 0.01 to 0.6 mM, preferably from 0.05 to 0.15 mM L-cysteine or salt thereof, per 1 ml of reagent, the remainder being water.

Control of the pH where required may be accomplished by addition of a convention buffer. The nature of the buffer is also not critical as long as the production of the binding protein is not prevented and the appropriate pH range is maintained. Suitable conventional buffers include a solution of from 0.001 to 250 mM Tris-acetate; from 0.01 to 50 mM magnesium acetate; and from 0.001 to 125 mM KCl (Buffer A); or a solution of from 0.001–250 mM $KH_2PO_4$ and from 0.01 to 50 mM magnesium acetate. For the specific formulation of the reagent mentioned above, up to 0.8 ml, preferably from 0.3 to 0.5 ml, of such buffers can be added per 1 ml of reagent.

It is also preferred that all solutions be formed using distilled and/or deionized water. Moreover, since ATP is so acidic it can be provided in the reagent from a stock solution having a pH closer to that desired for the final reagent, such as around 7.2. Adjustment can be achieved by addition of a compatible base such as KOH, NaOH and the like.

One of the three substrates should be tagged in some manner so that the binding protein in the reagent is readily detectable. Typically, radioactive tagging is used. Suitable tagging can be achieved by incorporation [$^{35}$S]—, or [$^{14}$C-U]-L-cysteine, [$^{14}$C]-D-pantothenic acid etc., in the reagent. ATP can also be tagged using its $\beta$-phosphorus group.

For the assay, a serum sample and the reagent are first mixed together, the order of mixing being non-critical. The relative amounts of the reagent and serum are not critical but should be chosen so that the serum protein/-binding protein complex is produced. For example, for the specific formulation described above, from 0.1 to 5.0 ml, preferably from 0.5 to 2.0 ml, of reagent per 0.01 to 0.30, preferably 0.04 to 0.06 ml of serum sample is suitable but other proportions are also usable. Of course, the ratio of the amount of reagent to the amount of serum sample will vary with the sensitivity of the radioactivity measurement; with the manner of performing the assay per se, e.g., automated vs. manual; with the specific composition of the reagent; with the specific technique used in the assay itself, e.g., the particular filtration methods used etc.; and other similar considerations.

After the mixing of the reagent and serum sample, the mixture is allowed to react to produce a sufficient amount of serum protein/B-protein complex for subsequent measurement in the assay. The reaction can be conventionally aided, for example, by incubation. The incubation conditions are chosen to enhance the appropriate reaction to form the complex without denaturing the active ingredients. An infinite variety of time and temperature combinations are of course possible. The lower the temperature the longer the incubation must be to produce amounts of binding protein complex equal to that produced at higher temperatures, and vice versa. The choice of the incubation conditions is not critical and is determined by considerations by convenience, expense, efficiency, time, detection sensitivity, etc. Thus, quite low temperatures can be used if the attendant long incubation times are acceptable. Typical incubation conditions include the use of temperatures of from 0° to 40° C., preferably 30°-37° C., for from 1.5 to 3.5 hours.

Once the serum protein/binding protein complex has been produced, partial denaturation of the complex is used to discriminate between normal serum protein/-binding protein complex and B-protein/binding protein complex. This denaturation differentially alters these two complexes so that the binding protein/B-protein complex will be denatured significantly more or less than is its normal serum protein counterpart, generally more. Which complex is denatured to the greater degree depends somewhat on the denaturation technique used. In general, any conventional denaturation technique should be applicable. For example, a heating treatment can be used and/or a chemical denaturation agent, such as trichloroacetic acid (TCA) and other similar conventional agents, can be added to the protein complex-containing solution. Of course, the complexes should only be partially denatured so that a significant difference in the amounts of denatured complexes (B-protein/binding protein vs normal protein/binding protein) exists permitting detection of the presence of the B-protein. This difference in solubility, i.e., denaturation properties, could be due to subtle differences in configuration and charge of the B-protein, which may be influenced by the location, type and extent of the malignancy. It appears, however, that if the progression of the malignancy is directly related to charge and configurational changes in this protein, it is relatively small, because very large percentages of the cancer patients studied, as shown in the Examples (89% to 87%), had a detectable level of serum B-protein with approximately the same solubility characteristics regardless of extent, type or location of the malignancy.

A typical denaturation procedure in accordance with the above requirements comprises heating the aforementioned incubation reagent/serum sample mixture to a temperature such as from 65° to 100° C., preferably 68° to 70° C. for from 1-10 minutes, preferably 3-6 minutes. Employment of such high temperatures also serves to terminate the incubation reaction. After cooling the solution, e.g., to less than 30° C., measurement of the amount of denatured protein can be performed at this time, but because of the large amount of endogenous and other non-protein-complex protein which is denatured initially it is preferred to first remove the denatured protein at this time, e.g., by filtration or centrifugation (e.g., at 2,000 to 2,300 rpm for from 4 to 6 min). Most of the yeast protein is thus removed as a precipitate. The supernatant liquid or filtrate contains the radioactively labeled binding protein/normal protein complex and the labeled binding protein/B-protein complex if the serum was from a cancer patient, or just the former, if the serum was from a non-cancer patient.

Thereafter, effective descrimination between the two complexes can be performed by additional partial denaturation, e.g., by addition of a conventional denaturation reagent such as TCA, alcohols and the like. For example, for the specific formulation described above, from 0.1 to 5 ml, preferably 1 to 2 ml, of a from 1 to 50% solution of denaturation agent (e.g., TCA) per ml of supernatant liquid or filtrate can be added, preferably with agitation.

At this stage the two complexes will be denatured to different extents. The final step of the assay involves measurement of the total amount of complex which is denatured. Comparison with the results of similar assays on normal and cancerous control serum samples, as described below, enables determination of the presence of cancer. First, of course, the resulting protein precipitate (denatured protein complexes) is separated in a conventional manner from its still solubilized, undenatured counterpart, for example, by centrifugation or preferably by filtration. Suitable conventional filters include Whatman 3 MM filter paper discs and Millipore filters and the like. Conventional washing (e.g., 3 to 5 washes using 2 to 3 ml of water) and drying (e.g., at 80°-90° C. for from 10 to 20 minutes) of the precipitate should precede the denatured protein measurement. Of course, scorching must be avoided. The dried discs are then analyzed for the presence of denatured binding protein/serum protein complex in conventional fashion.

For example, when the binding protein is radioactively tagged, the dried filters can be transferred to scintillation liquid vials and the radioactivity level measured by scintillation counting. Comparison with control values of radioactivity levels allows ascertainment of the presence of B-protein and of cancer in the patients as follows.

For each set of unknown serum samples tested, predetermined equivalent normal serum and cancerous serum samples are run under identical conditions as controls. Typically, for the specific formulation and denaturation procedure described above the normal serum range is from 200 to 500 cpm, for example. The cancer serum range is typically 900 to 1500 cpm, for example. Sera which fall within the lower range are considered normal. Those in the higher range are considered cancerous. Whenever counts are close to the range limits, assays should be re-run. If no exact determination can be made, the serum should be considered "unknown". However, generally the counts are always obviously located in either the high or low range and little difficulty is encountered in differentiating normal from cancer samples. Variations in the radioactivity of the tagged substrate do not affect the assay accuracy since any changes in the radioactivity level are reflected in both the normal and cancerous controls.

Using this procedure, considerably less radioactivity and protein are trapped on the filters when B-protein is absent than when it is present due to the differing effects of the specific denaturation treatments on normal and B-protein. These effects differentially alter the proteins so that the binding protein/B-protein complex is adhered on the filter to a much greater degree than is the normal protein counterpart. This is theorized to be due to the fact that normal protein is more resistant to this denaturation by the heating/TCA treatments than is the B-protein. Consequently, B-protein is the lesser soluble protein after the treatment so that a greater quantity of the normal protein passes through the filter while more of the B-protein is trapped on the filter. Since approximately the same quantity of radioactively labeled binding protein interacts with the serum protein of individuals whether or not they have cancer, a higher level of radioactivity and protein is detectable on the filter when B-protein is present in the serum.

The serum samples are recovered from blood which has been allowed to coagulate and centrifuged to separate the packed cells from the serum. A typical procedure is described in Example 1. The serum should not be extensively hemolyzed, as indicated by a dark red color, because the attendant red colored species interferes with the assay by producing quenching of the radioactivity. Lipemic serum, however, does not interfere.

As indicated above, many modifications of the above assay procedures can also be employed. For example, after the incubation of the specifically formulated reaction mixture described above, the aforementioned appropriate amounts of denaturation agent are added as a first denaturation treatment which also serves to terminate the reaction. The mixture is subsequently subjected to denaturation by heating as described above, and subsequently cooled. The washing and filtering operations are then carried out. As a result of this reversal of the order of denaturation treatments, the levels of radioactivity detectable are reversed. Serum from patients with cancer register a lower level of radioactivity on the filter than do those without cancer. Comparisons with control values, analagous to those mentioned above, are carried out to perform the assay.

Another particularly preferred modification can also be used. The reagent is incubated as above but without addition of the serum sample. This procedure permits reaction of the CoA-SPC to form CoA and the low molecular weight protein. The resultant reaction mixture is then passed through a conventional molecular weight cutoff filter or column. The weight average molecular weight cut-off should be from 20,000 to 100,000, preferably 30,000 to 50,000, so that the low molecular weight binding protein is passed through. The resultant filtrate is then used as a reagent for assay in precisely the same way as the reagent described above except that shorter reaction incubation periods at the same temperatures can be used.

It is also possible to successively fractionally filter this filtrate to isolate the appropriate 8,000 to 18,000, preferably 10,000 to 15,000, molecular weight fraction for the binding protein. For example, this can be accomplished by passing this filtrate through a filter which passes only substances having molecular weights lower than 50,000. The resultant filtrate can then be passed through a filter passing only substances of molecular weights lower than 1,000. The resultant material collected on the filter is washed to purify the binding protein of interest.

The characteristics of the low molecular weight binding protein may be summarized as follows:

1. It interacts with B-protein of serum and its apparent counterpart in normal serum.
2. It is released from CoA-SPC during the course of reaction.
3. It has a molecular weight in the range of 10,000 to 15,000.
4. It has been shown to be a component of Bakers' yeast.
5. It is reasonably heat stable to temperatures of 70° C.
6. It has not been shown to bind with any protein other than B-protein under the conditions of the assay. The following proteins were used to test this property: albumin, steapsin, amniotic fluid proteins, spinal fluid proteins, human milk, cow's milk, α-globulin (human), fibrin, peptone, histones (IIA, III, IV), hemaglobin, RNase, pyruvate kinase, pepsin, casein, Jack bean meal, protein hydrolysate (commercial), urease, gramicidin, ribosomal protein and fibrinogen.
7. It has 4'-phosphopanthetheine bound to its structure.

The assay of this invention provides a screening test for detecting the presence of cancer in patients with approximately an 88% reliability as indicated by the data in the Examples. As the Examples further demonstrate the presence of other diseases and physical problems do not have a profound influence on the assay results. Consequently, when the assay was run on geriatric patients with more than one physical problem or disease, no higher percentage of false positives was recorded. This also implies that the assay is effective irrespective of age.

It is not presently known at what stage of cancer growth B-protein is first observed in the serum. As discussed in the Examples, it appears that the assay of this invention is capable of detecting the presence of cancer earlier than presently possible, thereby greatly increasing a patient's chance of being cured.

The results of the assay of this invention as shown in Tables 1 and 3 of the Examples is correlated to the specific type of histology of each malignancy. These cancers were characterized by various stages (0 through IV) of disease and many different sites of occurrence. Moreover, they occurred in patients with and without treatment or metastasis. The results demonstrate an 87-88% positive correlation between the B-protein assay and the clinical diagnosis of malignancy. In approximately 12% of these cases studied, a false negative test result was found. As mentioned, the cause for the false negative is not known. Since randomly collected samples were used in the Examples, many of the patients in question were not available for follow-up.

It would appear that the B-protein assay correlates very well with the clinical diagnosis of malignancy in the following tumor types which have been tested: adenocarcinoma, squamous cell carcinoma, glial, lymphomas, leukemia, endocrine and other unknown types. There have been no specific types of tumors histologically nor functionally which have been tested that have not been detected by the B-protein assay.

However, the data suggests a better correlation between the test and growths of internal origin, such as adenocarcinoma, glial tumor, endocrine gland malignancies, lymphoma and the ones with occult primary tumor sites. In such tumors of internal origin, this assay should play an increasingly important role in early cancer detection. In addition, when employed routinely for physical examinations where there are no symptomatic indications of cancer, this assay should prove to be even more effective in the detection of early cancer before normal clinical diagnositic procedures are followed because of a complaint or indication from the patient that illness is suspected.

The correlations decrease for tumors of squamous cell carcinoma of the cervix, skin and leukemia. Fortunately, these three malignancies can be diagnosed clinically at early stages by pap smear for cervical cancer, physical exam for skin cancer and blood test and symptomatology for leukemias. In any event, the B-protein assay is applicable to all cancer types tested.

Furthermore, each tumor type tested in the Examples was represented by the entire spectrum of that malignancy with regard to stage. There seems to be no correlation between false negatives and various stages of development of the disease. For example, some of the Stage 0 cervical carcinomas were positive and some Stage IV patients produced negative B-protein assay results. The negative results may be a function of how early in the course of the disease the B-protein appears, or possibly the B-protein may have been destroyed during the course of processing of some of the samples.

Having generally described this invention, a further understanding can be obtained by reference to certain specific examples which are provided herein for purposes of illustration only and are not intended to be limiting unless otherwise specified.

EXAMPLE 1

Patient Population

One thousand patients, both male and female, of all economic levels were included in Example 1. Most of the patients were in the age group between 30 and 70. Some patients, however, were as young as 13 and others were as old as 92.

Serum for Assay

Blood from each patient was collected in 10 ml red stoppered, silicone coated Vacutainer tubes. No anticoagulant was added. The clot that formed was removed, and the blood was centrifuged. Following centrifugation, a Seraclear plug (Technicon) was inserted to separate the packed cells from the serum. Serum which was extensively hemolyzed was discarded and a new sample collected. The red color caused by hemolysis interferes with the assay by producing quenching of the radioactivity measurement. Lipemic serum, however, does not appear to have a significant effect on the results of the assay. Serum could be stored at $-20°$ C. for several weeks or stored for longer periods of time at a cryogenic temperature of $-100°$ C. Normal and cancer controls were chosen by screening serum from a number of individuals with and without cancer. These controls were used to provide the range of values for both normal and cancer samples.

Preparation of the Coenzyme A-Synthesizing Protein Complex

(CoA-SPC) of Bakers' Yeast

CoA-SPC was prepared as described by Bucovaz et al (References 11 and 12). Three pounds of Bakers' yeast were crumbled and then frozen for four to six hours in an either $CO_2$ mixture. The frozen yeast was allowed to thaw, and residual ether and $CO_2$ were removed by vacuum. Fifteen grams of KCl were added to the homogenate, and the mixture was stirred at 0° C. to 4° C. for 17 hours. Following the stirring step, the homogenate was centrifuged for 20 min. at 7,700 xg, and the supernatant layer was decanted through several folds of cheesecloth. The volume of the crude extract varied between 350 and 375 ml, depending upon the water content of the yeast. The crude extract was stored at cryogenic temperatures of $-100°$ C. The CoA-SPC prepared as described retained capacity for synthesis of CoA and for the release of the binding protein for several months.

B-protein Assay Procedure

The reaction mixture described is one in which [$^{35}$S]-L-cysteine was used as the radioactive tracer (substrate). [$^{14}$C-U]-L-cysteine or [$^{14}$C]-D-pantothenic acid have been used in place of [$^{35}$S]-L-cysteine.

A reaction mixture containing the following components was used: 2 mM disodium ATP, pH 7.2; 0.5 ml buffer A, pH 7.2 (containing 0.05 M Tris-acetate, pH 7.2; 0.01 M magnesium acetate; 0.02 M KCl); 0.5 mM hemicalcium D-pantothenic acid; 0.02 mM [$^{35}$S]-L-cysteine (60,000 cpm); 0.05 ml of the yeast extract containing CoA-SPC and water to a total volume of 1 ml. To this reaction mixture was added 0.05 ml of the serum being tested, and the total mixture was incubated at 36° C. for 2 hours. The reaction was terminated by heating the tubes in a $H_2O$-bath at 68° C. to 70° C. for 5 min. The tubes were then cooled to room temperature followed by centrifugation at approximately 2,200 rpm for 5 min. in a Model CL International Clinical Centrifuge. This procedure removed most of the yeast protein as a precipitate. The remaining supernatant liquid of the reaction mixtures in which normal serum was added contained the [$^{35}$S]-binding protein-normal protein complex. Whereas, the supernatant liquid of the reaction mixtures in which serum from cancer patients was added contained both [$^{35}$S]-binding protein-normal protein and [$^{35}$S]-binding protein-B-protein. Two millimeters of 10% TCA were added to each tube containing the supernatant liquid, and the tubes were shaken to assure proper mixing of the TCA. The resulting protein precipitates, which were primarily serum protein, were recovered by filtration using a Millipore filtering apparatus and Whatman No. 3 MM paper discs. The precipitates collected on the discs were washed 4 times with approximately 2 ml of water per wash. The discs containing the serum protein precipitates were dried in an oven at $<100°$ C. Precautions were taken to prevent scorching the discs. The dried discs were then transferred to scintillation vials containing scintillation liquid described by Hoskinson and Khorana (1965), and the radioactivity levels were measured in a Nuclear Chicago liquid scintillation counter.

With each set of unknown serum samples tested, a set of predetermined normal serum and cancer serum samples were run as controls. The normal serum range was 200 to 500 cpm, for example. The cancer serum range was 900 to 1500 cpm, for example. Sera which fell within the lower range was considered normal. Those in the higher range were considered cancerous. Whenever counts were close to the range limits, the assay was re-run. If no exact determination could be made, the serum was labeled "unknown". However, generally the counts were obviously located in the high or low range and there was little difficulty in identifying normal from cancer samples.

Assay Results

As shown in Table 1, 322 of the patients studied were diagnosed as having cancer. Whereas, the patients listed in Table 2 were hospitalized for various other reasons.

Of the cancer patients included in this study, the B-protein assay gave a positive reaction for 287 of the 322, or agreed with the clinical diagnosis in 89% of the cases. Approximately 11% of the patients diagnosed as having cancer in the clinic did not show a detectable level of B-protein in their serum. A portion of this 11% may be the result of incorrect clinical diagnosis. The discrepancy, also present in Example 2 below, may be explained on the basis of preliminary data which indicate that in some instances the B-protein is destroyed during collection or storage of the serum sample.

The data of Table 2 show that 597 of the 678 patients in the control group have a negative B-protein value, and 81 patients from this group had positive values. Thus, 88% of this test group gave results indicating the absence of cancer. These patients, however, were being treated for other reasons, as indicated in Table 2. The diagnoses of 149 patients included in Table 2 were classified as unknown, but not suspected of having cancer. Some of the patients in this unknown group may have had cancer which was not detected because of diagnostic limitations. The category labeled miscellaneous included five patients with severe burns over 20% of their body area. All of the burn patients had a positive B-protein reading.

Overall, the test results were not in accordance with the clinical information provided in 116 of the 1000 patients, but were in agreement in the assessment of 884 cases or 88.4% of those tested.

TABLE 1

B-PROTEIN ASSAY RESULTS OF PATIENTS WITH CANCER

| Cancer Location or System[a] | Number in category | Test Results[b] Positive | Test Results[b] Negative | Positive % |
|---|---|---|---|---|
| Head and Neck | 27 | 25 | 2 | 92.59 |
| Castro-intestinal | 37 | 33 | 4 | 89.19 |
| Genito-urinary | 107 | 96 | 11 | 89.72 |
| Respiratory | 26 | 25 | 1 | 96.15 |
| Reticulo-endothelium | 29 | 26 | 3 | 89.66 |
| Integument | 9 | 7 | 2 | 77.78 |
| Breast | 45 | 35 | 10 | 77.78 |
| Other | 8 | 7 | 1 | 87.50 |
| Unknown | 34 | 22 | 1 | 97.06 |
| Total | 322 | 287 | 35 | 89.13 |

[a]Information provided by the physician or obtained from medical records
[b]A positive test result indicates the presence of cancer; a negative test result indicates the absence of cancer.

TABLE 2

B-PROTEIN ASSAY RESULTS OF PATIENTS IN CONTROL GROUP

| Patient Type[a] | Number in Category | Test Results[b] Positive | Test Results[b] Negative | Negative % |
|---|---|---|---|---|
| Cardiovascular | 28 | 1 | 27 | 96.43 |
| Orthopedic | 81 | 6 | 75 | 92.59 |
| Gynecological | 19 | 1 | 18 | 94.74 |
| Obstetrical | 246 | 32 | 214 | 86.99 |
| Surgical | 50 | 3 | 47 | 94.00 |
| Medical | 42 | 2 | 40 | 95.24 |
| Neurological | 32 | 4 | 28 | 87.75 |
| Miscellaneous | 31 | 9 | 22 | 70.97 |
| Unknown | 149 | 23 | 126 | 84.56 |
| Total | 678 | 81 | 597 | 88.05 |

[a]Information was provided by the physician or obtained from medical records
[b]A positive test result indicates the presence of cancer; a negative test result indicates the absence of cancer.

EXAMPLE 2

Patient Population

More than two thousand patients were included in this Example. Most of the patients were in the age group between 25 and 65. Of the 2,005 patients included, 586 were diagnosed as having cancer and 1,419 were being treated for other reasons. Tumor registry data were obtained on a random sampling of the cancer patients.

All procedures used in Example 1 were employed here except for the following.

Preparation of the Coenzyme A-Synthesizing Protein Complex (CoA-SPC) Bakers' Yeast The CoA-SPC was prepared by the method reported (Bucovaz et al, Reference 11). Three pounds of Bakers' yeast were crumbled and frozen for 4 to 6 hours in an ether-$CO_2$ mixture. The frozen yeast was allowed to thaw, and residual ether and $CO_2$ were removed by vacuum. Fifteen grams of KCl were added to the homogenate, and the mixture was stirred at 0° to 4° C. for 3 hours. This initial stirring procedure removed endogenous substrates from the CoA-SPC. 30 ml of the homogenate were transferred to another flask and stirred an additional 12 hours. This portion of the homogenate was used only as a basis to determine the degree of purification on the CoA-SPC. The remainder of the homogenate was centrifuged at 7,700 xg for 20 minutes and the supernatant liquid discarded. A volume of 1:10 dilution of buffer A (described under "B-protein Assay") equal to that of the discarded supernatant liquid was added to the pellets in the centrifuge tubes. The pellets were resuspended, centrifuged and the supernatant liquid discarded. The addition of buffer A was repeated, and the pellets were resuspended and pooled. Stirring of the resuspended pellet material was continued for an additional 12 hr. During this stirring procedure, CoA-SPC was progressively released from its cellular structural affinities.

Assay Results

As shown in Table 3, the 586 patients studied had been diagnosed as having cancer. Whereas, the patients listed in Table 4 were hospitalized for various other reasons. Of the cancer patients included in this study, the B-protein assay gave a positive reaction for 510 of the 586, or agreed with the clinical diagnosis in 87% of the cases. Approximately 13% of the patients diagnosed as having cancer in the clinic did not show a detectable level of B-protein in their serum as determined by the B-protein assay.

The data of Table 4 show that 1,306 of the 1,419 patients which were not diagnosed as having cancer gave a negative B-protein value, and 113 patients from this group had positive values. Included in this group were 50 heavy smokers, none of which had a positive level of B-protein. Thus, 92% of this test group shown in Table 4 gave results indicating the absence of cancer. Only serum from patients treated for severe burns over 20% of their body area, and serum from women during the third trimester of pregnancy gave an abnormally high positive test result.

Overall, the test results were not in accordance with the clinical information provided in 189 of the 2,005 patients, but were in agreement in the assessment of 1816 cases or 90% of those tested.

TABLE 3
B-PROTEIN ASSAY RESULTS OF CANCER PATIENTS

| Cancer Location or System[a] | Number of Patients in Category | Test Results[b] Positive | Negative |
|---|---|---|---|
| Breast | 69 | 55 | 14 |
| Endocrine | 10 | 9 | 1 |
| Gastro-Intestinal | 91 | 84 | 7 |
| Genito-urinary | 162 | 142 | 20 |
| Integument | 64 | 54 | 10 |
| Miscellaneous | 9 | 8 | 1 |
| Neurological | 5 | 3 | 2 |
| Respiratory | 47 | 43 | 4 |
| Reticulo-endothelium | 72 | 59 | 13 |
| Unknown | 57 | 53 | 4 |
| Total | 586 | 510 | 76 |

[a]This information was provided by the physician or obtained from medical records.
[b]A positive test result indicated the presence of cancer; a negative result indicated the absence of cancer.

TABLE 4
B-PROTEIN ASSAY RESULTS OF PATIENTS IN CONTROL GROUP

| Patients Type[a] | Number of Patients in Category | Test Results[b] Positive | Negative |
|---|---|---|---|
| Cardiovascular | 79 | 2 | 77 |
| Gynecological | 52 | 2 | 50 |
| Obstetrical | | | |
| Childbirth | 63 | 11 | 52 |
| Pregnancy | 279 | 33 | 246 |
| Orthopedic | 192 | 9 | 183 |
| Medical | 130 | 4 | 126 |
| Miscellaneous | | | |
| Burn | 5 | 4 | 1 |
| Others | 49 | 5 | 44 |
| Unknown | 291 | 28 | 263 |
| Neurological | 62 | 5 | 57 |
| Surgical | 167 | 10 | 57 |
| Total | 1,419 | 113 | 1,306 |

[a]This information was provided by the physician or obtained from medical records.
[b]A positive test result indicated the presence of cancer; a negative result indicated the absence of cancer.

It might be rationalized that age should be a prime factor in this assay because the older an individual becomes, the more likely that individual is to have other diseases and physical problems which might influence the assay. As the results of Examples 1 and 2 show, this did not prove to be the case. As indicated (Tables 2 and 4), other diseases and other physical problems did not have a profound influence on the results of the assay.

At present there is insufficient information to determine the stage of cancer development which results in formation of the B-protein. Some cancer patients appear to have a higher ratio of B-protein to its normal protein counterpart in their serum than other patients. There are some indications that B-protein production may take place during the early stage of cancer development. Of the patients studied, some had very early signs of abnormal changes in cell structure; whereas, in other patients, the cancer was in a more advanced stage of development. In most of the patients studied, however, morphological changes in the tissues were apparent to the extent that cancer had been diagnosed or suspected prior to assay of the serum. It is unlikely that cancer must develop to the initial stage of metastasis before detection is possible by this assay procedure. If the initial stage of metastasis must be reached, then in some cases, initiation of the metastatic event must take place in cancerous tissue much earlier than presently believed. In any event, the B-protein assay most certainly appears to have the potential to detect most cancers of internal origin much earlier than they would presently be recognized.

EXAMPLE 3

The following procedures were used to both characterize the nature of the assay and to assure its effectiveness and validity.

Assay for CoA-SPC Release Activity

The composition of the reaction mixture used to assay for CoA-SPC binding protein release activity was the same as described under "B-Protein Assay Procedure" except serum was omitted from the mixture. 20 ml of the reaction mixture were incubated at 36° C. Samples were removed for assay at 30 min intervals during the course of a 150 min incubation period. Termination of the reaction of each sample removed for assay was accomplished by the addition of 2 ml of 10% TCA and heating the samples at 95° C. for 5 min. The tubes were then cooled in an ice bath, and the precipitates were recovered by filtration using a Millipore filtering apparatus and Whatman No. 3 MM paper discs. The precipitates collected on the discs were washed 4 times with approximately 2 ml of water per wash. The discs were dried in an oven at <100° C. and then transferred to scintillation vials for radioactivity determination.

Following the 150 min incubation period, another sample was removed from the reaction flask and applied to a column of Sephadex G-200 and eluted with buffer A at a flow rate of 1 ml per min.

Determination of Protein

Protein concentration was determined by the method of Lowry et al, J. Biol. Chem., 193, 265-275 (1951).

Gel Filtration

Approximately 40 g of Sephadex G-200, coarse (Pharmacia), were equilibrated for 4 days in buffer A. A column (2.5×60 cm) was prepared from the material and allowed to settle for 2 days. The column was kept at 0°-4° C. The CoA-SPC was eluted using buffer A at a flow rate of 1 ml per min.

Support for Protein-Protein Interaction

One hundred ml of a reaction mixture with the same concentration of components as described under "B-Protein Assay," but without serum, were incubated for 2 hr at 36° C. Following incubation, the reaction mixture was divided into two equal parts. One-half of the mixture was filtered using Amicon Centriflo cones with a cut-off rate of 50,000 molecular weight. The other half of the reaction mixture was filtered using an Amicon untra-filtration membrane UM-2 with a cut-off rate of 1,000 molecular weight.

Each filtrate was tested individually in the B-protein assay by adding one ml of the filtrate to each of a series of tubes containing serum to be assayed. The mixtures were then incubated at 36° C. for 30 min. Following the incubation, the reaction was terminated by heating the tubes at 68° C. to 70° C. for 5 min. and the remainder of the procedure described under "B-protein Assay" was followed.

For the CoA-SPC to be functional in the B-protein assay, experimental evidence supports the contention that the CoA-SPC must have release activity for the low molecular weight protein (binding protein). Evidence for protein-protein interaction between the binding protein and either the B-protein or its normal counterpart is highly suggestive, but not conclusive. However, all evidence accumulated thus far would support a protein-protein interaction. Of course, this theory is not meant to limit this invention in any way.

Each filtrate was added individually to a second series of tubes containing serum to be assayed. Also added individually to these reaction mixtures was 0.20 mM L-cysteine, D-pantothenic acid, ATP, CoA, dephospho-CoA, pantetheine and 4'-phosphopantetheine as possible inhibitors of the reaction.

The approximately 5-fold excess of L-cysteine, D-pantothenic acid, ATP, CoA, dephospho-CoA, pantetheine and 4'-phosphopantetheine, when added to the reaction medium, did not interfere with the B-protein assay. This would be expected if the B-protein assay is a protein-protein interaction between the B-protein of serum and the radioactively labeled binding protein. If some other radioactively labeled 4'-P-pantetheine were being transferred from the yeast binding proteing to the B-protein, it might be expected that the unlabeled components added to the reaction mixture would interfere with the B-protein assay.

Additional evidence in support of the binding protein being the functional product of CoA-SPC in the B-protein assay was provided by filtering the other one-half of the reaction mixture through an Amicon UM-2 membrane (1000 molecular weight cut-off). This filtration permitted the passage of only low molecular weight components of the reaction mixture into the filtrate. In this case the filtrate, which did not contain radioactively labeled binding protein, was not functional in the B-protein assay.

Molecular Weight Determination

The Sephadex G-200 column prepared as described above was used. The total bed volume, inner gel volume, volume of gel, and void volume of the column were determined. A calibration curve (Andrew, Biochem J., 91, 222-223(1964), was used to estimate the molecular weight of the complex, the binding protein, B-protein and the specific protein of normal serum which interacts with the binding protein. The calibration curve was obtained by chromatographing a mixture of glutathione (Sigma Chemical), bovine serum albumin (Sigma Chemical), bovine pancreas α-chymotrypsin (Sigma Chemical), and bovine ribonuclease (Sigma Chemical).

Inhibition of CoA-SPC Activity

Inhibition of CoA-SPC activity was determined as described under "Assay for CoA-SPC Release Activity" except the incubation time was 1 hr., and 0.20 mM CoA, dephospho-CoA, pantetheine and 4'-phosphopantetheine were added individually to reaction mixtures.

RESULTS

Not all preparations of CoA-SPC release binding protein which is needed for the function of the B-protein assay. Thus, each new preparation of CoA-SPC was tested in the following ways to determine if binding protein release activity was present.

Profile of CoA-SPC with Functional Release Activity

The time course of CoA-SPC bound radioactivity is shown in FIG. 1. For this study [$^{35}$S]-L-cysteine was used as the radioactive substrate. The experimental procedure was the same as described under "Assay for CoA-SPC Release Activity." As shown in FIG. 1, a 5 to 6 min delay was observed before a measurable amount of protein-bound radioactivity, representing dephospho-CoA formation, was detected. This lag period was followed by a linear increase, which in turn was followed by a leveling-off period. In the majority of CoA-SPC preparations in which release activity was functional, a significant decrease in the level of bound radioactivity was observed during the second hr of incubation (broken line, FIG. 1). With some preparations of CoA-SPC which have lost release activity, the plateau region of the curve was maintained throughout the second hr of incubation (solid line, FIG. 1). These two patterns were also seen if [$^{14}$C]-D-pantothenic acid or [$^{14}$C]-ATP was used in place of [$^{35}$S]-L-cysteine as the radioactive substrate in the experiment.

Following the 150 min incubation period, another sample of the reaction mixture was removed from the reaction flask and applied to a column of Sephadex G-200.

Gel Filtration

Figure 2:
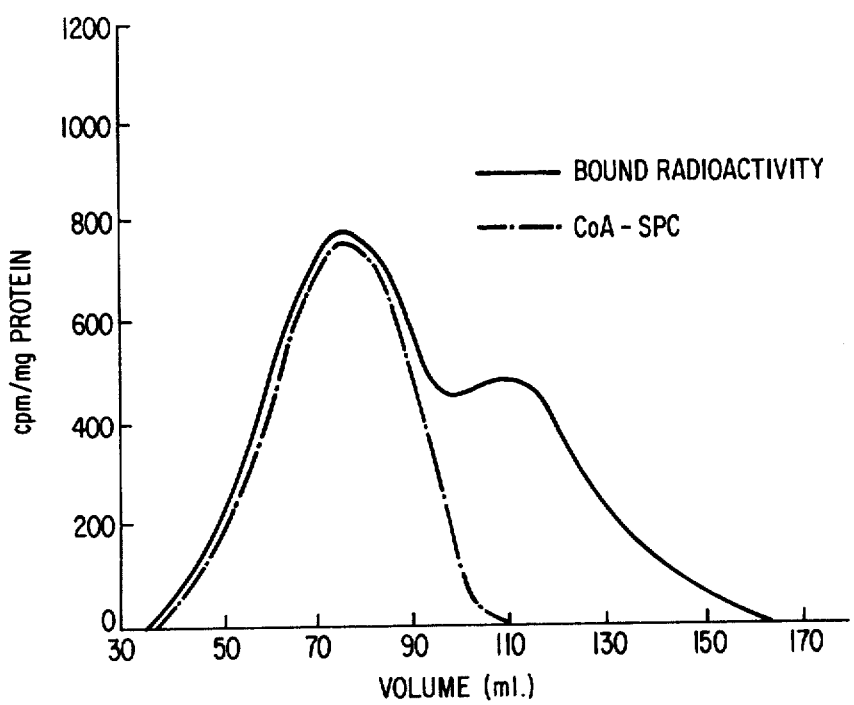
FIG. 2 shows the gel filtration pattern of CoA-SPC (— · —) having release activity, of protein (- - -) and of bound radioactivity (—).

The Sephadex G-200 elution pattern of a reaction mixture in which CoA-SPC with release activity was used is shown in FIG. 2. Column fractions collected were assayed for protein by the method of Lowry et al. and for radioactivity. As shown, two peaks of radioactivity were eluted from the column. One peak containing the major portion of the protein and radioactivity was eluted in fractions 33 through 100. The second fraction of radioactivity was bound to a protein of lower molecular weight (fractions 106-160).

Utilizing the method described by Andrew, the higher molecular weight component which represented the CoA-SPC had an estimated molecular weight in excess of 200,000, and the lower molecular weight protein (binding protein) had an estimated molecular weight of 10,000-15,000. A similar elution pattern to the one shown in FIG. 2 was obtained whenever [$^{14}$C]-D-pantothenic acid or [$^{35}$S]-L-cysteine was the radioactive substrate in the experiment. CoA-SPC preparations which did not show the decrease in radioactivity during the second hour of incubation, FIG. 1, also did not show the presence of binding protein released from CoA-SPC (FIG. 2). Only CoA-SPC preparations which exhibited release activity for the binding protein were functional in the B-protein assay.

Effect of Reaction Products and Related Compounds on CoA-SPC Activity

Reaction products and compounds with related structures were tested as inhibitors of CoA-SPC bound dephospho-CoA formation as described under "Inhibition of CoA-SPC Activity." CoA, dephospho-CoA, pantetheine and 4'-phosphopantetheine at a concentration of 0.20 mM inhibited CoA-SPC activity at least 90%.

Effect of Reaction Components and Products on B-Protein Assay

The procedure described under "Support for Protein-Protein Interaction" was followed. The radioactively labeled binding protein and other low molecular weight components were collected in the filtrate obtained by filtering a reaction mixture using Amicon Centriflo cones with a cut-off rate of 50,000 molecular weight.

Another filtrate was obtained which did not contain the binding protein, but contained reaction components of molecular weight of 1,000 or less by filtering a reaction mixture using an Amicon ultrafiltration membrane UM-2. Only the filtrate containing radioactively labeled binding protein, when added to a series of tubes with serum to be assayed, provided a functional B-protein assay.

The addition of 0.20 mM L-cysteine, D-pantothenic acid, ATP, CoA, dephospho-CoA, pantetheine and 4'-pantetheine to assay mixtures which contained the filtrate that had radioactively labeled binding protein did not interfere with the B-protein assay.

Having now fully described this invention, it will be apparent to one of ordinary skill in the art that many changes and modifications can be made thereto without departing from the spirit or scope of the invention set forth herein.

What is claimed as new and desired to be secured by Letters Patent of the United States is:

1. Purified CoA-SPC Bakers' yeast extract characterized by a molecular weight of greater than 200,000 and by utilizing the substrates L-cysteine, D-pantothenic acid and ATP to produce CoA.

* * * * *